US012678323B2

(12) United States Patent
Von Hollen et al.

(10) Patent No.:  US 12,678,323 B2
(45) Date of Patent:       Jul. 14, 2026

(54) SYSTEM AND METHOD FOR INTERACTIVE ORAL APPLIANCE TO OPEN AND CLOSE MOUTH PERIODICALLY TO PREVENT DISCOMFORT AND MOUTH BREATHING

(71) Applicant: KONINKLIJKE PHILIPS N.V., Eindhoven (NL)

(72) Inventors: Dirk Ernest Von Hollen, Clark, NJ (US); Nicholas Ernest Genco, Pittsburgh, PA (US); Zachary Fortune, Pittsburgh, PA (US); Peter Douglas Hill, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 443 days.

(21) Appl. No.: 18/215,408

(22) Filed: Jun. 28, 2023

(65) Prior Publication Data

US 2024/0000603 A1      Jan. 4, 2024

Related U.S. Application Data

(60) Provisional application No. 63/357,061, filed on Jun. 30, 2022.

(51) Int. Cl.
*A61F 5/56*          (2006.01)
*A61B 5/00*          (2006.01)
(Continued)

(52) U.S. Cl.
CPC ............ *A61F 5/566* (2013.01); *A61B 5/4815* (2013.01); *A61B 5/4818* (2013.01); *A61B 7/003* (2013.01); *A61B 5/0816* (2013.01)

(58) Field of Classification Search
CPC ..... A61F 5/566; A61B 5/4815; A61B 5/4818; A61B 7/003; A61B 5/0816
See application file for complete search history.

(56) References Cited

U.S. PATENT DOCUMENTS 3,353,271  A      11/1967  Blechman
7,712,468  B2      5/2010  Hargadon
(Continued)

FOREIGN PATENT DOCUMENTS

CH          717118  A2      8/2021
CN      106618839  A      5/2017
(Continued)

*Primary Examiner* — James J Yang

(74) *Attorney, Agent, or Firm* — Brynne J. Corcoran

(57)          ABSTRACT

An intelligent oral appliance (100) comprises maxillary and mandibular appliances (102, 104), an electromagnetic clamp (106, 108), first and second sensors (110, 112), a timer (114), and a controller (116). The electromagnetic clamp (106, 108) couples between the maxillary (102) and mandibular (104) appliances and operates according to engaged and disengaged clamping actions. The first sensor (110) detects a body/head position/orientation. The second sensor (112) detects a characteristic of sleep disordered breathing, snoring intensity, or combination thereof. The timer (114) provides preset time intervals. The controller (116) controls activation and deactivation of the electromagnetic clamp (i) to activate the electromagnetic clamp (106, 108) and electromagnetically lock the maxillary appliance (102) and mandibular appliance (104) together for air flow prevention cycles in response to an initial powering ON of the intelligent oral appliance or detection of an engagement triggering event and (ii) to de-activate the electromagnetic clamp (106, 108) and unlock the maxillary appliance (102) from the mandibular appliance (104) for periodic relaxation cycles in response to detection of a disengagement triggering event.

20 Claims, 7 Drawing Sheets

(51) Int. Cl.
    *A61B 7/00*         (2006.01)
    *A61B 5/08*         (2006.01)

(56)              References Cited

U.S. PATENT DOCUMENTS

| | | | |
|---|---|---|---|
| 8,844,537 B1 * | 9/2014 | Abramson | A61B 5/4836 |
| | | | 607/42 |
| 11,191,663 B2 * | 12/2021 | Radmand | A61N 1/36139 |
| 11,484,434 B2 | 11/2022 | Ghuge et al. | |
| 2013/0239978 A1 * | 9/2013 | Stubbs | A61F 5/566 |
| | | | 128/861 |
| 2013/0284184 A1 | 10/2013 | Wagner | |
| 2021/0145628 A1 | 5/2021 | Ghuge | |
| 2021/0401614 A1 * | 12/2021 | Shin | A61B 5/1116 |
| 2022/0183879 A1 | 6/2022 | Peyman et al. | |

FOREIGN PATENT DOCUMENTS

| | | | | |
|---|---|---|---|---|
| EP | 2543027 | B1 | 8/2016 | |
| KR | 20130029184 | A | 3/2013 | |
| WO | 2007134375 | A1 | 11/2007 | |
| WO | 2020153561 | A1 | 7/2020 | |
| WO | 2022051566 | A1 | 3/2022 | |
| WO | WO-2024178222 | A2 * | 8/2024 | A61N 1/3611 |

\* cited by examiner

100

102

1

SYSTEM AND METHOD FOR INTERACTIVE ORAL APPLIANCE TO OPEN AND CLOSE MOUTH PERIODICALLY TO PREVENT DISCOMFORT AND MOUTH BREATHING

CROSS REFERENCE TO RELATED APPLICATION

This application claims the benefit of U.S. Provisional Patent Application Ser. No. 63/357,061, filed Jun. 30, 2022. This application is incorporated by reference herein.

BACKGROUND

The present embodiments relate generally to oral appliances and more particularly, to an intelligent interactive oral appliance and method to open and close a user's mouth periodically to prevent discomfort and mouth breathing.

Snoring occurs when vibrations of the pharyngeal airway create a respiratory sound during sleep. In addition, snoring is associated with sleep disorders like sleep apnea and hypopnea. However, it does not necessarily indicate the presence of a more serious sleep disorder. The prevalence of snoring has been estimated at 25-40% of the overall population.

Snoring is the hoarse or harsh sound that occurs when air flows past relaxed tissues in a person's throat, causing the tissues to vibrate as he or she breathe. Nearly everyone snores now and then, but for some people it can be a chronic problem. Snoring is typically most frequent and loudest when sleeping on the back as gravity's effect on the throat narrows the airway.

Various commercially available device solutions are available to address snoring. These devices include a group that targets keeping the mouth closed throughout the night. Chin straps and mouthpieces or oral appliances have been employed to keep an individual's mouth closed throughout the night. To treat Obstructive Sleep Apnea (OSA), a mandibular advancement device (MAD) forces the lower jaw forward which pulls the rear part of the tongue away from the soft pallete and the back of the oropharynx. The risk of the tongue causing a partial or full occlusion of airflow is reduced. However, the lower jaw may only need to be held in its normal awake position and not allowed to open or move anteriorly. This would also prevent airway closure in some cases and without risking joint pain common with MADs.

Common side effects of oral appliances may include drooling, temporomandibular disturbances (e.g., muscular or related to joint—also known as the TMJ), tooth pain, and movements of the teeth changing a person's bite. Symptoms of pain or discomfort that continue or worsen through the day, last more than a few weeks, or interfere with a patient's normal daily function, should be considered persistent and may hinder long-term adherence to an Oral Appliance Therapy (OAT).

Other systems employ the use of magnetic forces. U.S. Pat. No. 3,353,271 A describes the use of a magnetic element for anchoring as a latching means to continuously hold the teeth (i.e., upper and lower) together throughout the night. Controlling magnetic forces to change the individual's airway geometry have been described in U.S. Pat. No. 8,844, 537 which employs an electromagnetic operatively connected to the device that generates an electromagnetic field to widen an airway of the user in response to detecting the breathing anomaly while the user is asleep.

Recent advances have allowed for the incorporation of electronic sensors to monitor/control airways. European patent EP254392B1 describes a system which is to be worn in an oral cavity of an individual and includes a sensor carried by the oral appliance. In U.S. Pat. No. 7,712,468 B2, a removable magnetic dental appliance is described. The magnetic dental appliance can be used in the treatment of various conditions, including but not limited to, snoring, sleep apnea, some forms of temporomandibular joint (TMJ) pain or inflammation, myofascial pain, or bruxism. The appliance uses magnetic force to selectively position the mandible while still permitting movement of the mandible relative to the maxilla for improved comfort.

In the dental appliance disclosed in U.S. Pat. No. 7,712, 468 B2, a magnetic component is positioned anteriorly on one of the upper arch attachment member or the lower arch attachment member and a non-magnet magnet-attracted element is provided on the other arch attachment member for magnetic engagement with the magnetic component when the upper and lower arch attachment members are substantially vertically aligned.

The above-mentioned dental appliances suffer from various problems and disadvantages. For example, comfort related issues occur when using a therapy that requires the mouth to remain closed, resulting from prolong periods of keeping teeth together or the jaw locked into a single position. Such therapies further impact comfort issues which are associated with oral appliances and mouth guards. This leads to discomfort and is a major factor in an individual discontinuing therapy. Furthermore, fixed oral appliances which lock a user's jaw into place throughout the night can also lead to additional issues related to air not periodically flowing through oral cavity and buildup of salvia due to the presence of the oral appliance in the user's mouth.

Referring now to FIG. 1, a flow diagram is shown illustrating an example of a current use case of a typical sleep process 10. Sleep process 10 includes interruptions due to snoring without assistance of an oral appliance or other snoring mitigation device. The sleep process 10 begins with an individual and his/her bedpartner preparing to go to bed (Step 12), followed by getting into bed (Step 14) and falling to sleep (Step 16). After falling asleep, the individual settles into a given position and/or changes his/her position which corresponds with the supine position, on his/her back (Step 18). Subsequently, the individual's mouth falls open (Step 20), air moves into and out of the opening of the mouth (Step 22), upon which the individual begins snoring (Step 24). The sound of snoring disrupts the individual (Step 26), upon which the individual may experience aroused from sleep (Step 28). Similarly, the sound of the individual's snoring disrupts the bedpartner (Step 30), upon which the bedpartner may experience aroused from sleep (Step 32), and in response to the arousal, the bedpartner renders a physical motion or verbal communication to the individual for the individual to turn to his/her side (Step 34). At step 36, the individual responds to the sleep arousal, the physical motion, or the verbal communication, by changing position and turning to his/her side. Subsequently, the individual's mouth partially closes (Step 38). Air is redirected to flow in and out through the individual's nose (Step 40) and sleep resumes (Step 42). This process repeats itself, beginning with Step 18 and continuing until the individual awakens from his/her period of sleep.

Accordingly, an improved method and apparatus for overcoming the problems in the art is desired.

SUMMARY

According to one embodiment, an intelligent interactive oral appliance comprises a maxillary appliance, a mandibular appliance, at least one electromagnetic clamp, first and second sensors, a timer and a controller. The maxillary appliance is configured to be releasably secured to an upper dentition and the mandibular appliance is configured to be releasably secured to a lower dentition. The at least one electromagnetic clamp is coupled between the maxillary or mandibular appliances and configured to operate according to (i) an engaged clamping action in response to energization of the respective at least one electromagnetic clamp and (ii) a disengaged clamping action in response to de-energization of the respective at least one electromagnetic clamp. The first sensor is configured to detect at least one of a body position, a body orientation, a head position, a head orientation, or any combination of body and head positions or orientations (i.e., head/body position/orientation). The second sensor is configured to detect at least one of (i) a characteristic of sleep disordered breathing, (ii) a snoring intensity, or (iii) any combination thereof. The timer is configured to provide one or more preset time intervals. The controller is configured to control an activation and a deactivation of the at least one electromagnetic clamp between the engaged clamping action and the disengaged clamping action, respectively, (i) to activate the at least one electromagnetic clamp and electromagnetically lock the maxillary appliance and mandibular appliance together for one or more air flow prevention cycles in response to (i)(a) an initial powering ON of the intelligent oral appliance or (i)(b) detection of an engagement triggering event and (ii) to de-activate the at least one electromagnetic clamp and unlock the maxillary appliance from the mandibular appliance, respectively, for one or more periodic relaxation cycles in response to detection of a disengagement triggering event.

The intelligent interactive appliance further comprises wherein each electromagnetic clamp includes (i)(a) an electromagnet coupled to one of the maxillary or mandibular appliance at a posterior position thereof, and (i)(b) a metallic conductive material coupled to the other of the maxillary or mandibular appliance at a complementary posterior position thereof. The engaged clamping action corresponds with the electromagnet of a respective electromagnetic clamp electromagnetically engaging with and being clamped to the metallic conductive material of the respective electromagnetic clamp. The disengaged clamping action corresponds with the electromagnet of the respective electromagnetic clamp no longer being clamped to, but electromagnetically disengaged from, the metallic conductive material of the respective electromagnetic clamp.

In one embodiment, the electromagnet and the metallic conductive material of a respective electromagnetic clamp are each coupled on a same side of a respective maxillary or mandibular appliance at a posterior position thereof. In another embodiment, the electromagnet and the metallic conductive material of a respective electromagnetic clamp are each coupled to the maxillary or mandibular appliance at a posterior position thereof within a predetermined percentage of the total distance, back to front, from the posterior end of the respective maxillary or mandibular appliance.

According to another embodiment, the controller initiates (i) a first type of periodic relaxation cycle in alignment with a given sleep stage based upon one or more outputs of the first sensor, the second sensor, and the timer to minimize a disruption to sleep quality which may otherwise occur without the periodic relaxation cycle, and (ii) a second type of periodic relaxation cycle anytime within a sleep cycle based on the second sensor detecting (a) no snoring level activity or (b) a minimal snoring activity level or (c) one or more transient event needing relief, to allow de-activation of the electromagnetic clamp and unlock the maxillary appliance from the mandibular appliance and to allow, in the case of the transient event, momentary relief from a respective transient event. Still further, the controller initiates a periodic relaxation cycle in alignment with a predetermined head, body, or head and body position or orientation.

According to yet another embodiment, the intelligent oral appliance further comprises wherein the controller initiates the periodic relaxation cycle in response to one or more of (i) the first sensor detecting a predetermined head, body, or head and body position or orientation, (ii) the second sensor detecting a snore intensity less than a threshold intensity, and (iii) the at least one electromagnetic clamp not having been activated for a duration of at least a preset time interval. The preset time interval is reset upon (i) the initial powering ON of the intelligent oral appliance or (ii) a de-activation of the at least one electromagnetic clamp by a trigger other than detection of an upright position/orientation. In a further embodiment, the preset time interval is selected from the group consisting of fixed periods defined by a length of minutes, starting at 15 minutes up to a threshold time of no more than 60 minutes. In addition, the predetermined head, body, or head and body position or orientation is a non-supine position and/or orientation.

In another embodiment, the intelligent interactive oral appliance further comprises an additional sensor configured to detect a change in vibration or sound of a predetermined threshold amplitude associated with a beginning of a snoring event, and wherein the controller (a) terminates a given periodic relaxation cycle in response to detecting that the change in vibration or sound meets or exceeds the predetermined threshold amplitude associated with the beginning of the snoring event, and (b) subsequently re-activates the at least one electromagnetic clamp. In addition, the controller re-initiates the periodic relaxation cycle in response to (i) the electromagnetic clamp having not been re-activated during at least the preset time interval, and (ii) the first sensor detecting a head, body, or head and body position or orientation other than supine position. According to another embodiment, the intelligent oral appliance further comprises a power source adapted to provide power to the first, second, and additional sensors, the timer, and the controller.

In a further embodiment, the engagement triggering event comprises detection of one or more selected from the group consisting of a supine position, a snore intensity having an amplitude greater than a threshold, and expiration of a preset time interval. In addition, the disengagement triggering event comprises at least one of (i) detection of an upright position/orientation, and (ii) any combination of (a) no detection of a supine position, (b) no detection of a snore intensity having an amplitude greater than a threshold, (c) detection of a biological response to secretion or fluid buildup to a point that would be sensed for initiation of a cough or swallowing response action, or (d) no detection of expiration of the preset time interval. Furthermore, the preset time interval is a time interval that is reset upon (i) the initial powering ON of the intelligent oral appliance or (ii) the disengagement of the at least one electromagnetic clamp by a trigger other than detection of the upright position/orientation.

According to yet another embodiment, an intelligent interactive oral appliance comprises a maxillary and mandibular appliance, at least one electromagnetic clamp, first and second sensors, a timer, and a controller. The maxillary appliance is configured to be releasably secured to an upper dentition and the mandibular appliance is configured to be releasably secured to a lower dentition. The at least one electromagnetic clamp includes (i)(a) an electromagnet coupled to one of the maxillary or mandibular appliance and (i)(b) a metallic conductive material coupled to the other of the maxillary or mandibular appliance, wherein the electromagnetic clamp is configured to operate between (ii)(a) an engaged setting in which energization of the electromagnet produces a clamping action for electromagnetically engaging the metallic conductive material and (ii)(b) a disengaged setting in which de-energization of the electromagnet produces a non-clamping action for enabling the electromagnet to electromagnetically disengage from the metallic conductive material. The first sensor is configured to detect at least one of a body position, a body orientation, a head position, a head orientation, or any combination of body and head positions or orientations. The second sensor is configured to detect at least one of (i) a characteristic of sleep disordered breathing, (ii) a snoring intensity, or (iii) any combination thereof. The timer is configured to provide one or more preset time intervals.

The controller is configured to control an activation and a deactivation of the at least one electromagnetic clamp between the engaged setting and the disengaged setting, respectively, (i) to activate the at least one electromagnetic clamp and electromagnetically lock the maxillary appliance and mandibular appliance together for one or more air flow prevention cycles in response to (i)(a) an initial powering ON of the intelligent oral appliance or (i)(b) detection of an engagement triggering event and (ii) to de-activate the at least one electromagnetic clamp and unlock the maxillary appliance from the mandibular appliance, respectively, for one or more periodic relaxation cycles in response to detection of a disengagement triggering event. The engagement triggering event comprises detection of one or more selected from the group consisting of a supine position, a snore intensity having an amplitude greater than a threshold, and expiration of a preset time interval. The disengagement triggering event comprises at least one of (i) detection of an upright position/orientation, and (ii) any combination of (a) no detection of a supine position, (b) no detection of a snore intensity having an amplitude greater than a threshold, (c) detection of a biological response to secretion or fluid buildup to a point that would be sensed for initiation of a cough or swallowing response action, or (d) no detection of expiration of the preset time interval. The preset time interval is a time interval that is reset upon (i) the initial powering ON of the intelligent oral appliance or (ii) the disengagement of the at least one electromagnetic clamp by a trigger other than detection of the upright position/orientation.

In another embodiment, the intelligent interactive oral appliance further comprises an additional sensor configured to detect a change in vibration or sound of a predetermined threshold amplitude associated with a beginning of a snoring event. In that embodiment, the controller (a) terminates a given periodic relaxation cycle in response to detecting that the change in vibration or sound meets or exceeds the predetermined threshold amplitude associated with the beginning of the snoring event, and (b) subsequently re-activates the at least one electromagnetic clamp. In addition, the controller re-initiates the periodic relaxation cycle in response to (i) the electromagnetic clamp having not been re-activated for a duration of at least the preset time interval, and (ii) the first sensor detecting a head, body, or head and body position or orientation other than supine position.

According to yet another embodiment, a method for implementing control of an intelligent interactive oral appliance comprises providing a maxillary appliance configured to be releasably secured to an upper dentition; providing a mandibular appliance configured to be releasably secured to a lower dentition; providing at least one electromagnetic clamp that includes (i)(a) an electromagnet coupled to one of the maxillary or mandibular appliance and (i)(b) a metallic conductive material coupled to the other of the maxillary or mandibular appliance, wherein the electromagnetic clamp is configured to operate between (ii)(a) an engaged setting in which energization of the electromagnet produces a clamping action for electromagnetically engaging the metallic conductive material and (ii)(b) a disengaged setting in which de-energization of the electromagnet produces a non-clamping action for enabling the electromagnet to electromagnetically disengage from the metallic conductive material; providing a first sensor configured to detect at least one of a body position, a body orientation, a head position, a head orientation, or any combination of body and head positions or orientations; providing a second sensor configured to detect at least one of (i) a characteristic of sleep disordered breathing, (ii) a snoring intensity, or (iii) any combination thereof; providing a timer configured to provide one or more preset time intervals; and controlling, via a controller, an activation and a deactivation of the at least one electromagnetic clamp between the engaged setting and the disengaged setting, respectively, (i) to activate the at least one electromagnetic clamp and electromagnetically lock the maxillary appliance and mandibular appliance together for one or more air flow prevention cycles to prevent airflow through an oral cavity during use of the intelligent oral appliance in response to (i)(a) an initial powering ON of the intelligent oral appliance or (i)(b) detection of an engagement triggering event and (ii) to de-activate the at least one electromagnetic clamp and unlock the maxillary appliance from the mandibular appliance, respectively, for one or more periodic relaxation cycles in response to detection of a disengagement triggering event.

In a further embodiment, the method includes wherein the engagement triggering event comprises detection of one or more selected from the group consisting of a supine position, a snore intensity having an amplitude greater than a threshold, and expiration of a preset time interval, and wherein the disengagement triggering event comprises at least one of (i) detection of an upright position/orientation, and (ii) any combination of (a) no detection of a supine position, (b) no detection of a snore intensity having an amplitude greater than a threshold, (c) detection of a biological response to secretion or fluid buildup to a point that would be sensed for initiation of a cough or swallowing response action, or (d) no detection of expiration of the preset time interval, and wherein the preset time interval is a time interval that is reset upon (i) the initial powering ON of the intelligent oral appliance or (ii) the disengagement of the at least one electromagnetic clamp by a trigger other than detection of the upright position/orientation.

The embodiments of the present disclosure advantageously solve problems as discussed herein. A primary problem solved is that of discomfort. The embodiments of the present disclosure overcome discomfort issues associated with prior known appliances that keep the mouth closed extended periods of time. As discussed, prolonged periods of mouth closure can disadvantageously lead to an individual discontinuing therapy. Overcoming the discomfort issues thus advantageously promotes improved therapy adherence.

A secondary problem overcome by the embodiments of the present disclosure is overcoming an impact on sleep quality to the user and/or bed partner from snoring. In this regard, the embodiments of the present disclosure advantageously provide a means to allow for periodic relaxation periods in relationship to body/head position (associated to supine) and a controlled means to re-close the mouth that allows controlled intermittent muscle relief throughout the night with minimal disturbance to individual and/or bed partner. For example, some configuration of prior known devices might be able to allow an individual to overcome a minimum force to keep mouth closed (e.g., as described in U.S. Pat. No. 7,712,468 B2 for a Magnetic Snore device) by allowing the magnetic force to be broken when the individual applies excessive force to break the magnetic attraction. However, such an approach leaves it to chance to engage the clamp which does not address a controlled means to ensure engagement occurs prior to disturbance of sleep due to increase snoring levels impacting sleep quality of the user and/or bed partner. The embodiments of the present disclosure advantageously provide a means of controlling when opening and closing a user's mouth in order to reduce the impact on sleep quality to themselves and bed partner from snoring.

Still further advantages and benefits will become apparent to those of ordinary skill in the art upon reading and understanding the following detailed description.

BRIEF DESCRIPTION OF THE DRAWINGS

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

DETAILED DESCRIPTION

Figure 1:
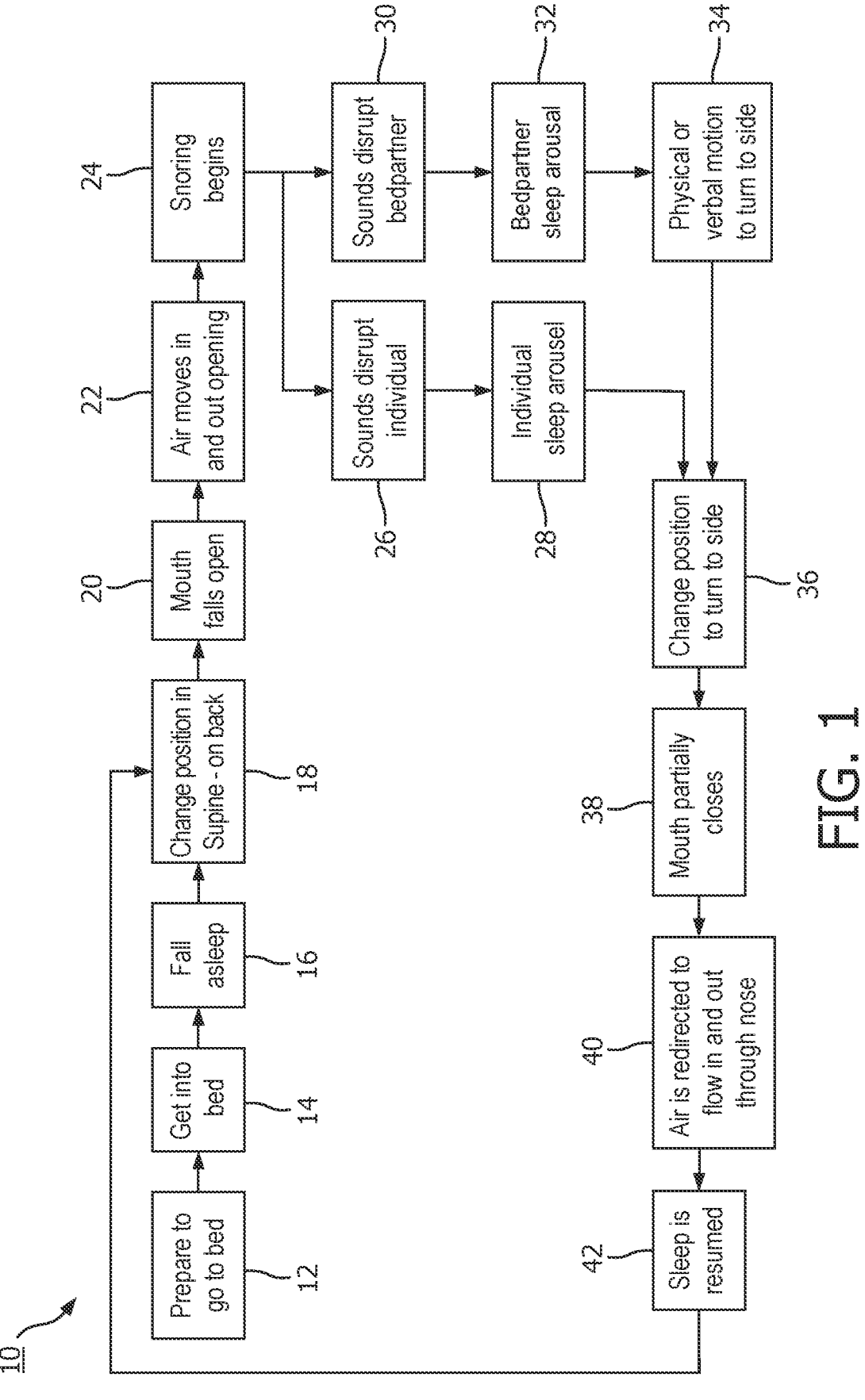
FIG. 1 is a flowchart of a current use case of a sleep process without use of device according to an embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

Figure 2:
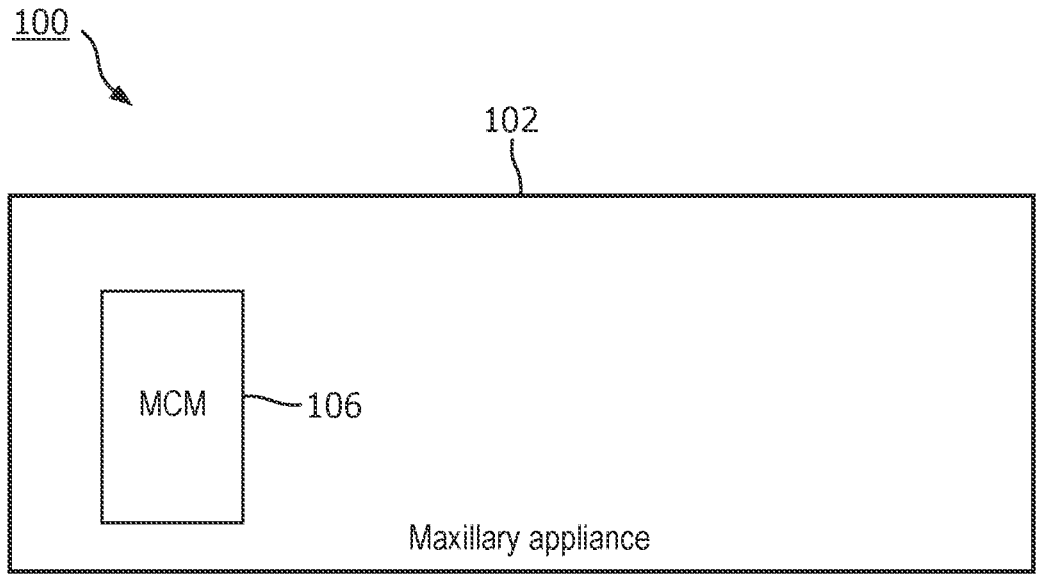
FIG. 2 is a block diagram representation of an intelligent interactive oral appliance according to an embodiment of the present disclosure.
Figure 2:
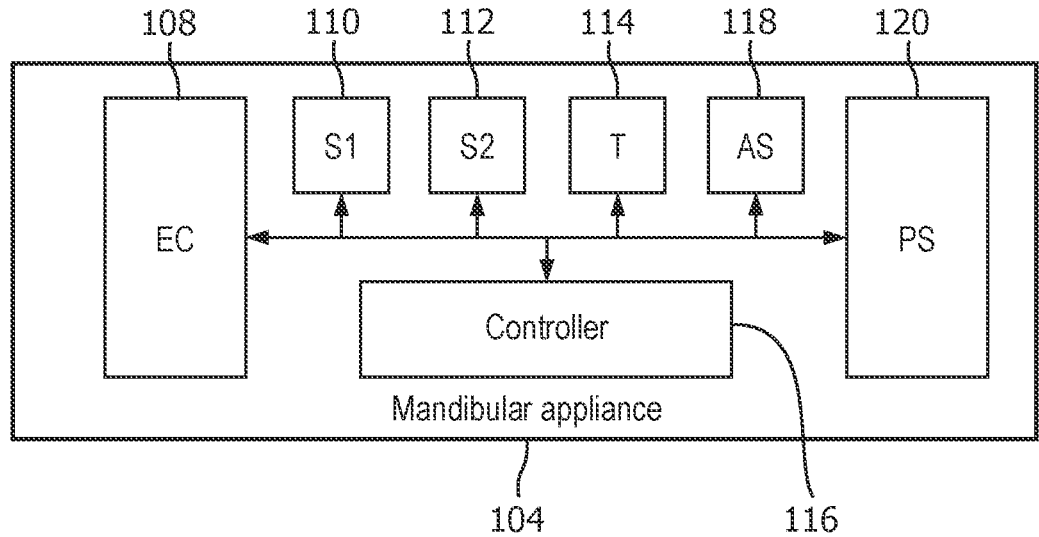

Turning now to FIG. 2, an intelligent interactive oral appliance 100 comprises a maxillary appliance 102, a mandibular appliance 104, at least one electromagnetic clamp (i.e., MCM and EC which are indicated via reference numerals 106 and 108), first and second sensors (S1 and S2) indicated by reference numerals 110 and 112, respectively, a timer 114 and a controller 116. The maxillary appliance 102 is configured to be releasably secured to an upper dentition 103 (or upper teeth, see FIGS. 3 and 4) and the mandibular appliance 104 is configured to be releasably secured to a lower dentition 105 (or lower teeth, see FIGS. 3 and 4). Additional configurations are contemplated. For example, the maxillary appliance and mandibular appliance can be releasably fitted to, be releasably engaged, or be positioned securely on, respective upper and lower dentitions. An additional configuration could be an entire replacement assembly (instead of an assembly secured onto the teeth that is removable) for removable denture on either maxillary or mandibular or both. In any case, the entire intelligent interactive appliance 100 is removable from an individual's mouth by the individual when not in use, i.e., for storage, cleaning or recharging (as will be discussed further herein).

As can be understood based on the present disclosure, both the maxillary appliance 102 and the mandibular appliance 104 are manually inserted and removed by the individual user when not in use. The electromagnet 108 and controller 116 (or electronic control circuit) have the capability to charge and discharge, allowing a controlled clamping action to engage and disengage with metallic conductive material 106. Both the metallic conductive material 106 and electromagnet 108 will be located near the hinge of the jawbone during use. The location of the electromagnet 108 minimizes the distance for electromagnetic clamping action.

As disclosed herein, the distance between the top and bottom bridges near the hinge of the jawbone is at its minimum and is important to engage when the user's mouth is periodically opened to minimize the amount of charge required to close. If located closer to the front of the mouth, the electromagnetic clamp (106, 108) would require a stronger magnetic force to engage due to the larger gap. This means a larger charge would need to be placed on electromagnet 108 to attract towards the metallic conductive material 106, which would need to be induced using a larger electric current generation. This increased distance (i.e., larger gap) would also result in a greater magnetic force engaging the mouthpieces (MP), which could result in sleep disturbances for the user.

The at least one electromagnetic clamp (106, 108) is coupled between the maxillary or mandibular appliances. While the drawings illustrate only one electromagnetic clamp (106, 108) on a same side of a respective maxillary or mandibular appliance (102, 104) at a posterior position thereof (e.g., proximate a posterior/distal end in a region of the hinge of a user's jawbone), another electromagnetic clamp (not shown) can be similarly disposed on an opposite side of the respective maxillary or mandibular appliance, which operates in unison with the first electromagnetic clamp.

Figure 3:
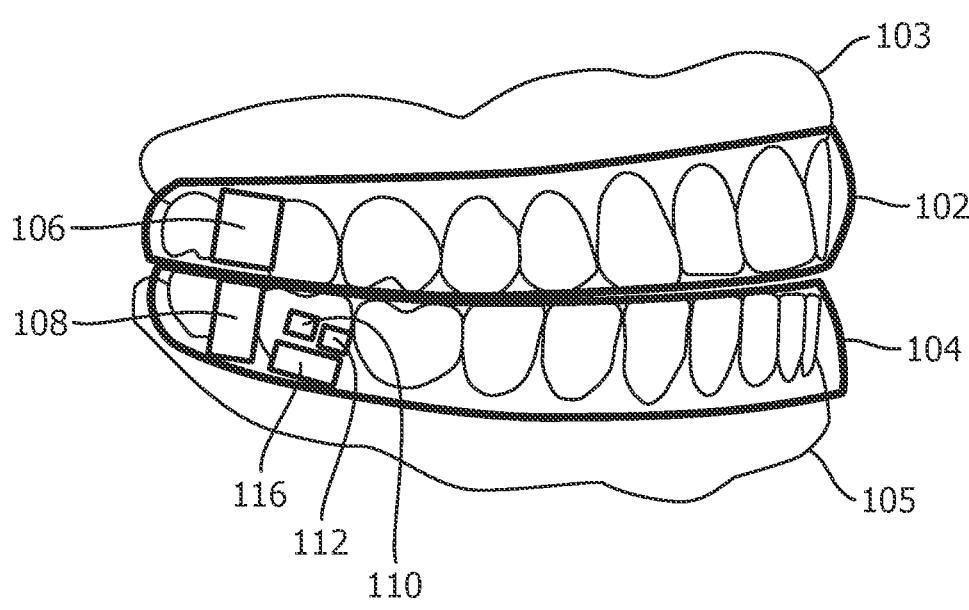
FIG. 3 is a partial block diagram view of an intelligent oral appliance in an engaged position according to an embodiment of the present disclosure.
Figure 4:
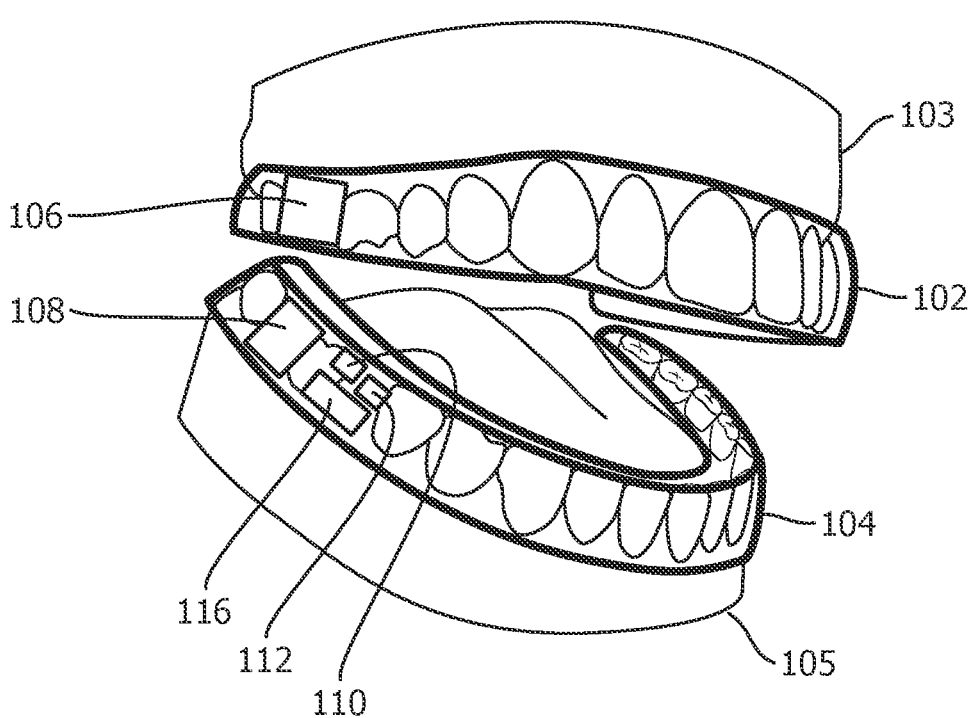
FIG. 4 is a partial block diagram view of an intelligent oral appliance in a disengaged position according to an embodiment of the present disclosure.

The at least one electromagnetic clamp (106, 108) is coupled between the maxillary or mandibular appliances 102 and 104, respectively, and configured to operate according to (i) an engaged clamping action in response to energization of the respective at least one electromagnetic clamp (FIG. 3) and (ii) a disengaged clamping action in response to de-energization of the respective at least one electromagnetic clamp (FIG. 4). Each electromagnetic clamp includes (i)(a) an electromagnet 108 coupled to one of the maxillary or mandibular appliance (102 or 104, respectively) at a posterior position thereof, and (i)(b) a metallic conductive material 106 coupled to the other of the maxillary or mandibular appliance at a complementary posterior position thereof. In one embodiment, the metallic conductive material 106 is encapsulated with a thin layer of polymer material. Other types materials for use in encapsulation may be possible.

According to another embodiment, the electromagnet 108 and the metallic conductive material 106 of a respective electromagnetic clamp are each coupled to the maxillary or mandibular appliance at a posterior position thereof within a predetermined percentage of the total distance, back to front, from the posterior end of the respective maxillary or mandibular appliance. For example, in one embodiment, the predetermined percentage is within 40% of the total distance, back to front, from the posterior end of the respective maxillary or mandibular appliance.

With reference among FIGS. 2, 3 and 4, the at least one electromagnetic clamp (106, 108) is configured to operate according to (i) an engaged clamping action in response to energization of the respective at least one electromagnetic clamp (FIG. 3) and (ii) a disengaged clamping action in response to de-energization of the respective at least one electromagnetic clamp (FIG. 4). In particular, the engaged clamping action corresponds with the electromagnet 108 of a respective electromagnetic clamp electromagnetically engaging with and being clamped to the metallic conductive material 106 of the respective electromagnetic clamp (FIG. 3). The disengaged clamping action corresponds with the electromagnet 108 of the respective electromagnetic clamp no longer being clamped to, but electromagnetically disengaged from, the metallic conductive material 106 of the respective electromagnetic clamp.

The first sensor (S1) 110 is configured to detect at least one of a body position, a body orientation, a head position, a head orientation, or any combination of body and head positions or orientations (i.e., head/body position/orientation) of the individual who is using the intelligent interactive oral appliance 100. The first sensor 110 comprises any suitable sensor adapted to detect one or more parameters according to a given intelligent interactive oral appliance application implementation. In one embodiment, the first sensor 110 comprises a barometric sensor to identify when an individual moves from a P t position (e.g., laying head on pillow) to a $2^{nd}$ position for sitting up to cough or getting out of bed. In another embodiment, the first sensor 110 comprises a three-axis (3-axis) accelerometer to identify orientation and head/body movement when moving from one orientation or movement to another to identify when an individual is in supine position.

The second sensor (S2) 112 is configured to detect at least one of (i) a characteristic of sleep disordered breathing, (ii) a snoring intensity, or (iii) any combination thereof of the individual who is using the intelligent interactive oral appliance 100. The second sensor 112 comprises any suitable sensor adapted to detect one or more parameters according to a given intelligent interactive oral appliance application implementation. In one embodiment, the second sensor 112 comprises a microphone that could detect into the ultrasonic range for changes in sounds related to obstructive or restrictive air flow turbulence resulting from airway collapse or obstruction by bodily fluids such as saliva or mucus secretion. Sound type could be determined by combination using measurements of decibel (dB) intensity or frequency profile, as an example. The timer (T) 114 is configured to provide one or more preset time intervals.

The controller 116 is configured to control an activation and a deactivation of the at least one electromagnetic clamp (106, 108) between the engaged clamping action (FIG. 3) and the disengaged clamping action (FIG. 4), respectively, (i) to activate the at least one electromagnetic clamp (106, 108) and electromagnetically lock the maxillary appliance 102 and mandibular appliance 104 together for one or more air flow prevention cycles in response to (i)(a) an initial powering ON of the intelligent oral appliance 100 or (i)(b) detection of an engagement triggering event and (ii) to de-activate the at least one electromagnetic clamp (106, 108) and unlock the maxillary appliance 102 from the mandibular appliance 104, respectively, for one or more periodic relaxation cycles in response to detection of a disengagement triggering event.

According to an embodiment, controller 116 comprises one or more of microprocessors, microcontroller, field programmable gate array (FPGA), integrated circuit, discrete analog or digital circuit components, hardware, software, firmware, or any combination thereof, for performing various functions as discussed herein, further according to the requirements of a given intelligent interactive oral appliance implementation and/or application. Controller 116 can further comprise one or more various executable modules configured for performing functions of the given intelligent interactive oral appliance implementations as disclosed herein. In addition, one or more of modules can further comprise various combinations of one or more of the various modules.

Figure 5:
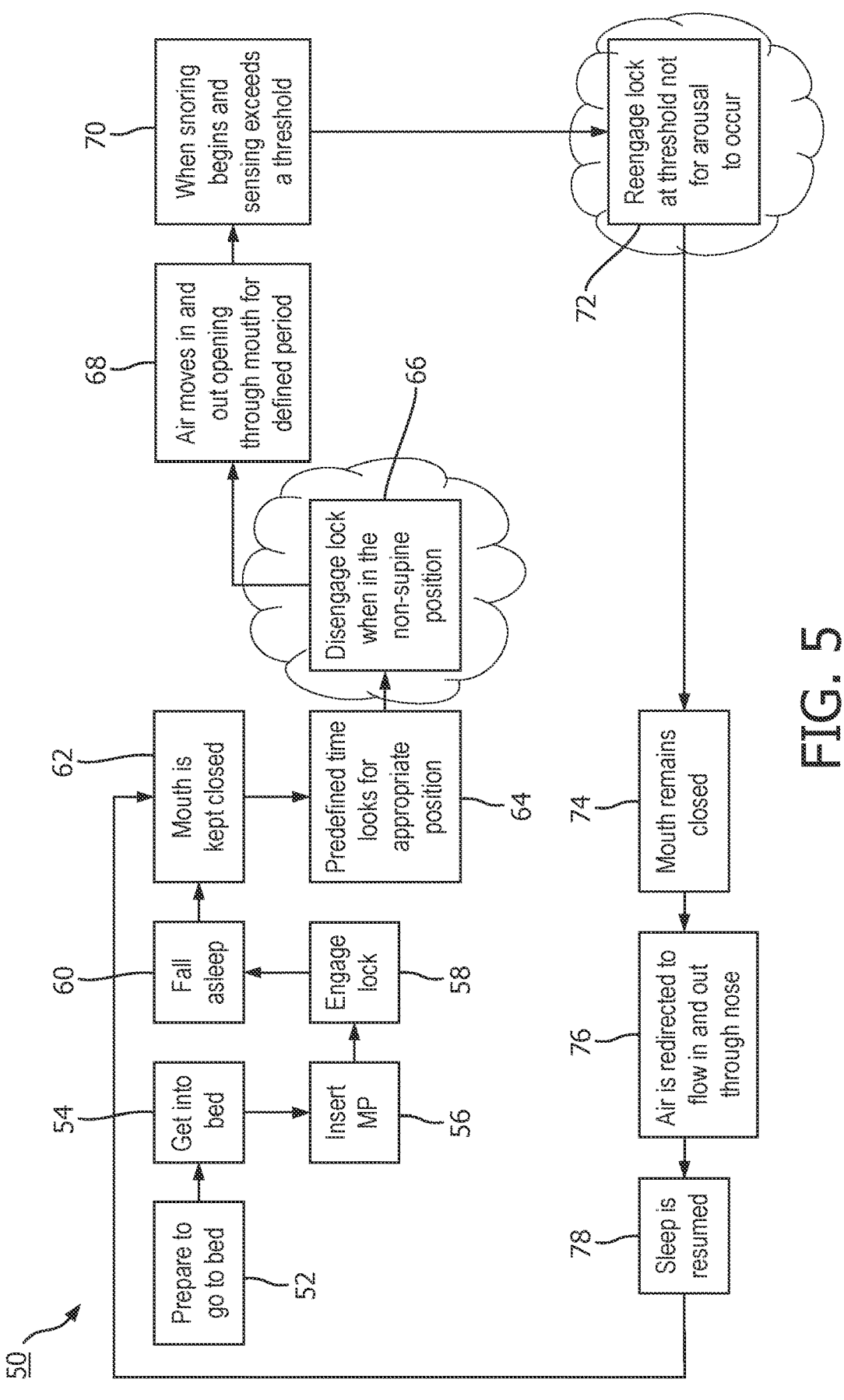
FIG. 5 is a flowchart of a use case of a sleep process that includes use of an intelligent oral appliance according to an embodiment of the present disclosure.

With reference now to FIG. 5, there is shown a flowchart of a use case of a sleep process 50 that includes use of an intelligent oral appliance according to an embodiment of the present disclosure. Sleep process 10 that includes interruptions due to snoring without assistance of an oral appliance.

The sleep process 50 begins with an individual preparing to go to bed (Step 52), followed by getting into bed (Step 54) and inserting the intelligent oral appliance (also referred to herein as a mouthpiece, MP), as will be discussed further herein, according to the embodiments of the present disclosure, into the user's mouth (Step 56). In one embodiment, the intelligent oral appliance includes a maxillary appliance and a mandibular appliance. The maxillary appliance is for being releasably secured to the top or upper teeth and the mandibular appliance is for being releasably secured to the bottom or lower teeth during use. The intelligent oral appliance further includes at least one electromagnetic clamp, as will be discussed further herein.

Subsequent to inserting the intelligent oral appliance into the individual's mouth, the at least one electromagnetic clamp of the intelligent oral appliance is engaged (Step 58). Engagement is carried out via an activation of the at least one electromagnetic clamp, and electromagnetically locking the maxillary appliance and mandibular appliance together for an air flow prevention cycle. In particular, the intelligent oral appliance is adapted to keep the individual's mouth closed to prevent air flow moving through the user's mouth for one or more air flow prevention cycles, as will be discussed further herein. The intelligent oral appliance can be used with or without flow or pressure support therapy (PAP, Oxygen, High Flow Oxygen, NIV delivered via an external nasal interface).

The individual then falls asleep (Step 60) and his/her mouth is kept closed, via the intelligent oral appliance (Step 62). After falling asleep, the individual settles into a given position and/or changes his/her position over time. Upon the passage of a predefined amount of time from when the intelligent oral appliance first engages the at least one electromagnetic clamp to keep the user's mouth closed, the intelligent oral appliance then monitors for a predetermined appropriate position of the asleep individual (Step 64). In response to detecting that the user's position is in a non-supine position, a position other than the user lying the user's back, then a dis-engagement is carried out (Step 66). The dis-engagement is carried out via a de-activation of the at least one electromagnetic clamp, and electromagnetically un-locking the maxillary appliance and mandibular appliance from one another for a relaxation cycle, as will be discussed further herein.

Having dis-engaged the maxillary appliance and the mandibular appliance, the individual may or may not open his/her mouth during the relaxation cycle. Assuming that the individual opens his/her mouth, the process continues with air moving in and out of the opening of the user's mouth for a predefined period of time (Step 68), after the dis-engagement began. In a next step, the individual may begin snoring and a snoring threshold may be exceeded (Step 70). That is, snoring is monitored and determined whether the sensing exceeds a threshold. Upon detection of the snoring exceeding a threshold, the process operates to re-engage the at least one electromagnetic clamp of the intelligent oral appliance is engaged (Step 72).

Re-engagement is carried out via activation of the at least one electromagnetic clamp, and electromagnetically locking the maxillary appliance and mandibular appliance together for another air flow prevention cycle. The user's mouth is thereupon closed and kept closed, via the intelligent oral appliance (Step 74). Subsequent to the user's mouth being closed again, the process continues with air being redirected (i) from moving in and out of the opening of the user's mouth to (ii) flow in and out through the user's nose (Step 76). Sleep resumes (Step 78) the process repeats itself with a return of the user's mouth being held closed via the intelligent oral appliance (Step 62). Subsequent to the user's mouth being closed, the process again monitors for a predetermined appropriate position of the asleep individual (Step 64) for a predefined period of time since the beginning of the re-engagement. This portion of the process repeats itself, beginning with Step 62 and continuing until the individual awakens from his/her period of sleep and the intelligent oral appliance is removed from the user's mouth.

With reference still to FIG. 5, as well as to FIGS. 2-4, in one embodiment, a respective air flow prevention cycle is adapted for keeping a user's mouth closed to prevent air flow moving through the user's mouth when used with or without flow or pressure support therapy (e.g., positive airway pressure (PAP), Oxygen, High Flow Oxygen, non-invasive ventilation (NIV) delivered via an external nasal interface (not shown)). In addition, a respective periodic relaxation cycles can be adapted for implementing controlled periods of disengagement of the at least one electromagnetic clamp (106, 108) to offset user discomfort to jaw muscle, teeth pain, a need to shallow buildup of saliva in the mouth, or a cough response.

In another embodiment, the controller 116 initiates (i) a first type of periodic relaxation cycle in alignment with a given sleep stage based upon one or more outputs of the first sensor 110, the second sensor 112, and the timer 114 to minimize a disruption to sleep quality which may otherwise occur without the periodic relaxation cycle, and (ii) a second type of periodic relaxation cycle anytime within a sleep cycle based on the second sensor 112 detecting (a) no snoring level activity or (b) a minimal snoring activity level or (c) one or more transient event needing relief, to allow de-activation of the electromagnetic clamp (106, 108) and unlock the maxillary appliance 102 from the mandibular appliance 104 and to allow, in the case of the transient event, momentary relief from a respective transient event. In one embodiment, the controller 116 initiates a periodic relaxation cycle in alignment with a predetermined head, body, or head and body position or orientation, wherein the predetermined head and/or body position and/or orientation comprises a user laying in a position/orientation other than supine position.

In one example, the intelligent oral appliance 100 addresses an additional need which requires a second type of periodic relaxation cycle (i.e., a variable periodic relaxation cycle). The second type of periodic relaxation cycle would be required anytime within the sleep cycle (i.e., not necessarily a sleep stage) when the second sensor 112 detects (a) no snoring or (b) minimal snoring activity level or (c) the detection of one or more transient event. A transient event is one requiring momentary deactivation of the electromagnetic clamp (106, 108), thereby allowing a momentary mouth opening or an airflow leak. The momentary deactivation advantageously allows for a momentary mouth opening or airflow leak (e.g., with respect to a PAP or other therapy) to relieve a need to cough or need to shallow.

In another embodiment, the controller 116 initiates the periodic relaxation cycle in response to one or more of (i) the first sensor 110 detecting a predetermined head, body, or head and body position or orientation, (ii) the second sensor 112 detecting a snore intensity less than a threshold intensity, and (iii) the at least one electromagnetic clamp (106, 108) not having been activated for a duration of at least a preset time interval, wherein the preset time interval is reset (i.e., started over) upon (i) the initial powering ON of the intelligent oral appliance or (ii) a de-activation of the at least one electromagnetic clamp by a trigger other than detection of an upright position/orientation. In one embodiment, the preset time interval is selected from the group consisting of fixed periods defined by a length of minutes, starting at 15 minutes up to a threshold time of no more than 60 minutes.

With respect to sleep cycles, a first ($1^{st}$) full sleep cycle is often shortest, ranging from 70-100 minutes, while later sleep cycles tend to fall between 90 and 120 minutes. The preset time interval is configured to allow the relaxation of muscles in the mouth (e.g., masseter muscles (or chewing muscles)) on a periodic basis within a typical sleep cycle and can be selectable by the individual, via any suitable means for selecting a time interval among a number of predetermined time intervals. In one embodiment, the preset time interval is selected from the group consisting of fix periods defined by length of minutes starting at 15 minutes up to a threshold time of no more than 60 minutes.

With reference again to FIG. 2, according to one embodiment, the intelligent interactive oral appliance 100 further comprises an additional sensor (AS) 118 and a power source (PS) 120. The additional sensor 118 is configured to detect a change in vibration or sound of a predetermined threshold amplitude associated with a beginning of a snoring event, and wherein the controller 116 (a) terminates a given periodic relaxation cycle in response to detecting that the change in vibration or sound meets or exceeds the predetermined threshold amplitude associated with the beginning of the snoring event, and (b) subsequently re-activates the at least one electromagnetic clamp (106, 108). In one embodiment, the additional sensor 118 can also be configured to detect snoring and/or another event. The other event can comprise, for example, a therapy leakage being provided by a secondary therapy apparatus (not shown) which is applied nasally (e.g., via oxygen cannula, PAP interface, NIV interface or High Flow Nasal Cannula). In a further embodiment, the controller 116 re-initiates the periodic relaxation cycle in response to (i) the electromagnetic clamp (106, 108) having not been re-activated during at least the preset time interval, and (ii) the first sensor 110 detecting a head, body, or head and body position or orientation other than supine position.

Still further, in one embodiment, the power source 120 comprises a rechargeable power source adapted to provide electrical power to the first, second, and additional sensors (110, 112, 118, respectively), the timer 114, and the controller 116. In one embodiment, the power source comprises a rechargeable battery configuration built onto the intelligent oral appliance 100. In another embodiment, the power source 120 comprises the use of a Near Field to energize the at least one electromagnetic clamp (106, 108) from an external source mounted on the skin near a location of the at least one electromagnetic clamp when the intelligent oral appliance is in use within a user's mouth.

According to a further embodiment, wherein the engagement triggering event comprises detection of one or more selected from the group consisting of a supine position, a snore intensity having an amplitude greater than a threshold, and expiration of a preset time interval, and wherein the disengagement triggering event comprises at least one of (i) detection of an upright position/orientation, and (ii) any combination of (a) no detection of a supine position, (b) no detection of a snore intensity having an amplitude greater than a threshold, (c) detection of a biological response to secretion or fluid buildup to a point that would be sensed for initiation of a cough or swallowing response action, or (d) no detection of expiration of the preset time interval. The preset time interval can comprise a time interval that is reset (i.e., started over) upon (i) the initial powering ON of the intelligent oral appliance or (ii) the disengagement of the at least one electromagnetic clamp by a trigger other than detection of the upright position/orientation or detection of a biological response to secretion or fluid buildup to a point that would be sensed at the initiation a cough or shallowing response action.

According to yet another embodiment, an intelligent interactive oral appliance 100 comprises a maxillary and mandibular appliance (102 and 104, respectively), at least one electromagnetic clamp (106, 108), first and second sensors (110 and 112, respectively), a timer 114, and a controller 116 as previously discussed herein with the following differences. The electromagnetic clamp (106, 108) is configured to operate between (a) an engaged setting in which energization of the electromagnet produces a clamping action for electromagnetically engaging the metallic conductive material and (b) a disengaged setting in which de-energization of the electromagnet produces a non-clamping action for enabling the electromagnet to electromagnetically disengage from the metallic conductive material.

The controller 113 is configured to control an activation and a deactivation of the at least one electromagnetic clamp (106, 108) between the engaged setting and the disengaged setting, respectively, (i) to activate the at least one electromagnetic clamp (106, 108) and electromagnetically lock the maxillary appliance (102) and mandibular appliance (104) together for one or more air flow prevention cycles in response to (i)(a) an initial powering ON of the intelligent oral appliance 100 or (i)(b) detection of an engagement triggering event and (ii) to de-activate the at least one electromagnetic clamp (106, 108) and unlock the maxillary appliance (102) from the mandibular appliance (104), respectively, for one or more periodic relaxation cycles in response to detection of a disengagement triggering event. The engagement triggering event comprises detection of one or more selected from the group consisting of a supine position, a snore intensity having an amplitude greater than a threshold, and expiration of a preset time interval. The disengagement triggering event comprises at least one of (i) detection of an upright position/orientation, and (ii) any combination of (a) no detection of a supine position, (b) no detection of a snore intensity having an amplitude greater than a threshold, (c) detection of a biological response to secretion or fluid buildup to a point that would be sensed for initiation of a cough or swallowing response action, or (d) no detection of expiration of the preset time interval. The preset time interval is a time interval that is reset upon (i) the initial powering ON of the intelligent oral appliance or (ii) the disengagement of the at least one electromagnetic clamp by a trigger other than detection of the upright position/orientation.

Figure 6:
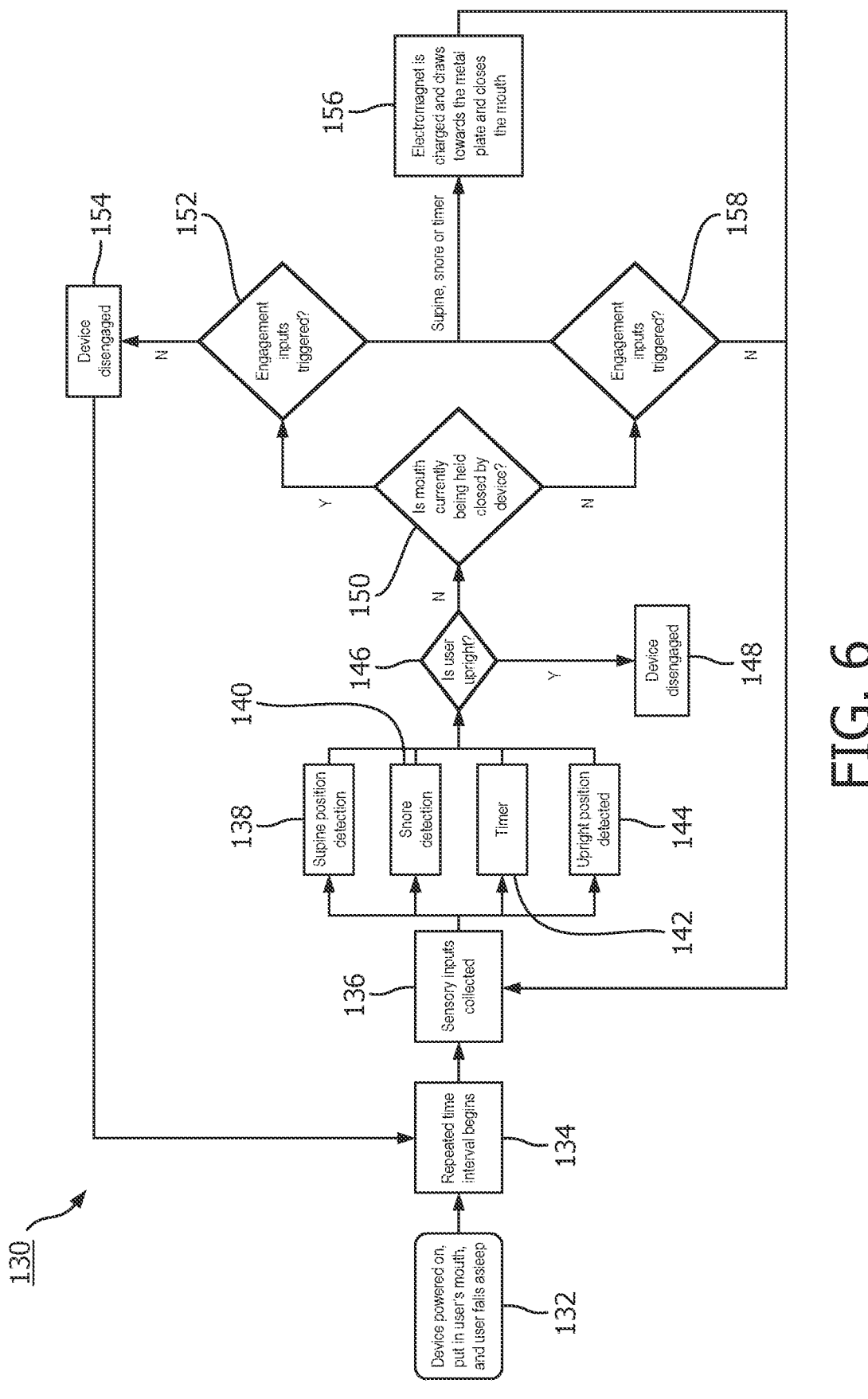
FIG. 6 is a flowchart of the method of operating the intelligent oral appliance in accordance with an embodiment of the present disclosure.
Figure 7:
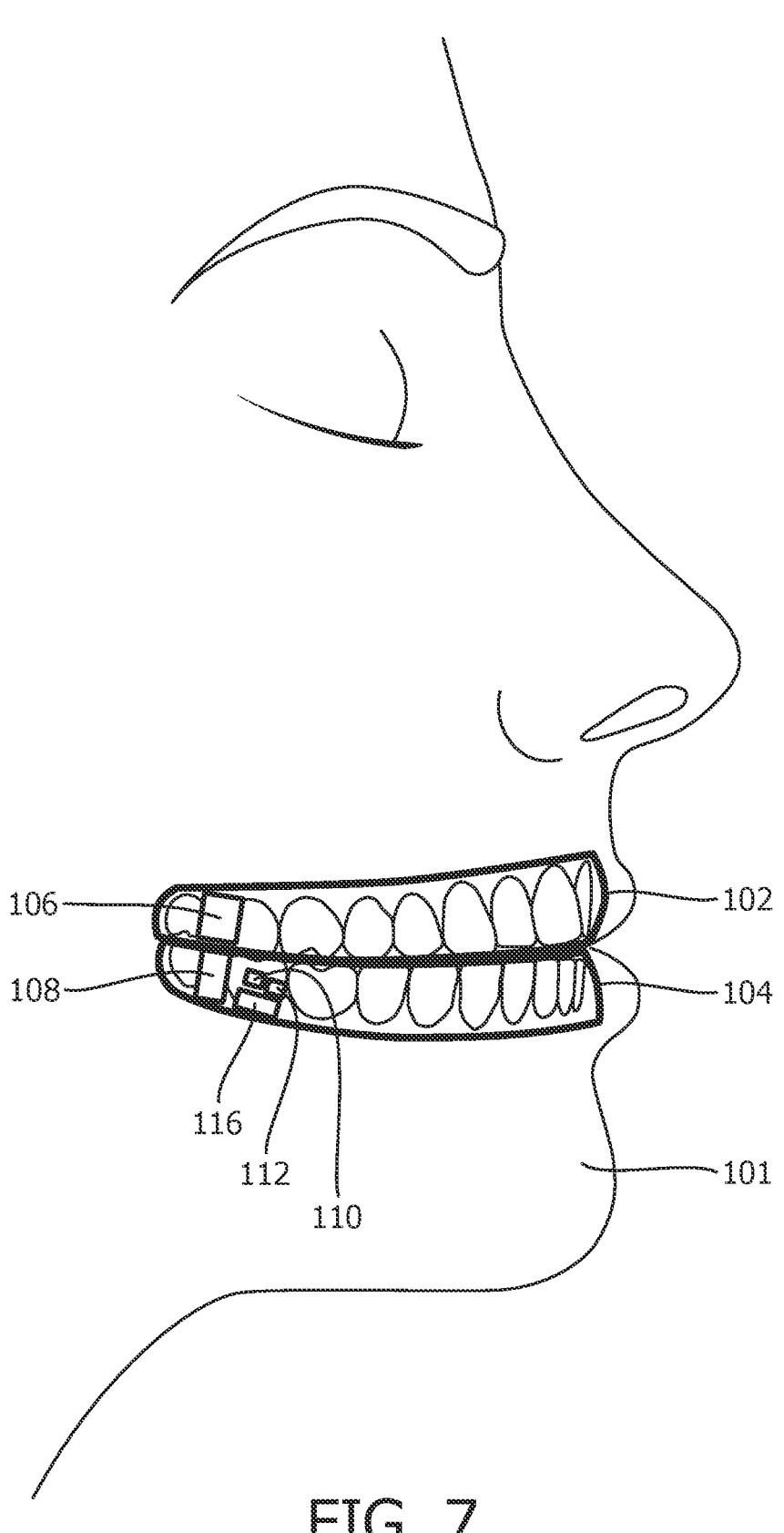
FIG. 7 is a partial block diagram view of an intelligent oral appliance in an engaged position in a user's mouth according to an embodiment of the present disclosure.
Figure 8:
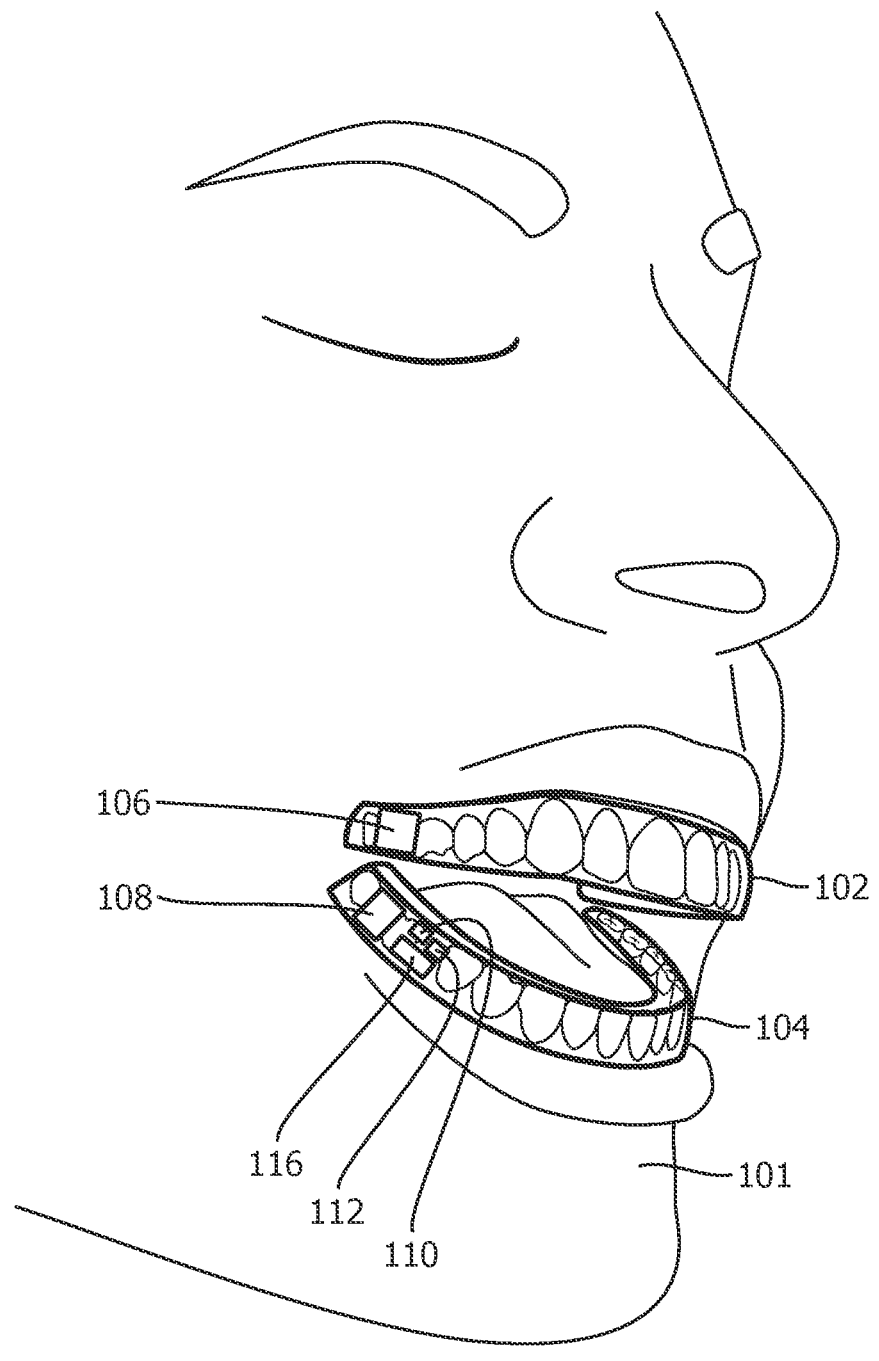
FIG. 8 is a partial block diagram view of an intelligent oral appliance in a disengaged position in a user's mouth according to an embodiment of the present disclosure.

With reference now to FIGS. 6, 7 and 8, a method 130 of operating the intelligent interactive oral appliance in accordance with an embodiment of the present disclosure will now be discussed. Method 130 begins with the intelligent interactive oral appliance 100 being powered ON, put into the user's mouth, and the user subsequently falling asleep (Step 132). At Step 134, a repeated time interval begins, via timer 114. The time interval corresponds with a given predetermined time interval. At Step 136, sensory inputs are collected, via first and second sensors (110 and 112, respectively) and optionally, via additional sensor 118. Step 138 includes supine position detection, via the controller 116 or a suitable module thereof. Step 140 includes snore detection, via controller 116 or a suitable module thereof. Step 142 includes monitoring time, via timer 114. Step 144 include upright position detection or other detection, e.g., of a biological response to secretion or fluid build-up as discussed herein, via controller 116 or a suitable module thereof. The method continues at Step 146 with a query whether the user is in an upright position. If the detection reveals that the user is in the upright position (e.g., a disengagement event), the method proceeds to Step 148. At Step 148, the at least one electromagnetic clamp is disengaged, via the controller 116. The process then proceeds again to Step 136, whereby sensory inputs are again collected. The process then repeats itself beginning with Step 136.

On the other hand, at query Step 146, in response to the user not being upright, the method continues at Step 150 with a query, via controller 116, whether the user's mouth is currently being held closed by the intelligent interactive oral appliance 100. In response to the user's mouth not currently being closed by the intelligent interactive oral appliance 100 (e.g., another disengagement event), the method proceeds at Step 152 with a query, via controller 116, whether engagement inputs have been triggered. In the event that engagement inputs have not been triggered, the method proceeds at Step 154 by disengaging the at least one electromagnetic clamp (106, 108). Subsequent to Step 154, the method proceeds back to Step 134, whereby the repeated time interval is begun again, via timer 114. The process then repeats itself beginning with Step 134.

With reference still to FIG. 6, at Step 152, in the event that engagement inputs have been triggered (e.g., supine, snore, or timer), then the method proceeds at Step 156. Step 156 includes engaging, via the controller, the at least one electromagnetic clamp (106, 108), and more particularly, energizing the electromagnet 108, via controller 116 and power source 120, for drawing the conductive metal plate 106 towards the electromagnet 108 and closing, or maintaining closed, the user's mouth (FIG. 7). The process then proceeds again to Step 136, whereby sensory inputs are again collected. The process then repeats itself beginning with Step 136.

With reference again to Step 150, this step is a query whether the user's mouth is currently being held closed by the intelligent interactive oral appliance 100. In response to the query, via controller 116, when it is determined that the user's mouth is not currently being held closed by the intelligent interactive oral appliance 100, then the process proceeds to Step 158. Step 158 includes a query, via controller 116, whether engagement inputs have been triggered. In the event that engagement inputs have not been triggered, the method proceeds again to Step 136, whereby sensory inputs are collected. The process then repeats itself beginning with Step 136. by disengaging the at least one electromagnetic clamp (106, 108). Subsequent to Step 154, the method proceeds back to Step 134, whereby the repeated time interval is begun again, via timer 114. The process then repeats itself beginning with Step 134.

Referring still to FIG. 6, at Step 158, in the event that engagement inputs have been triggered (e.g., supine, snore, or timer), then the method proceeds at Step 156. Step 156 includes engaging, via the controller, the at least one electromagnetic clamp (106, 108), and more particularly, energizing the electromagnet 108, via controller 116 and power source 120, for drawing the conductive metal plate 106 towards the electromagnet 108 and closing, or maintaining closed, the user's mouth (FIG. 7). The process then proceeds again to Step 136, whereby sensory inputs are again collected. The process then repeats itself beginning with Step 136.

In other words, as a user prepares for bed, the system or intelligent interactive oral appliance is charged and both the maxillary and mandibular appliances are insert into their mouth and securely mounted on the associated teeth regions. The mandibular appliance is active and engages the electromagnet to engage with the maxillary appliance containing the metallic conductive material ultimately holding the mouth closed when the head is in the lateral position. The system is disengaged when the user's head is upright as a convenience and comfort feature for the user.

Once together, this activates the controller and timer. The controller (or control circuit) will monitor for conditions to periodically disengage and allow the mouth to open. These conditions are dependent on the position the user is sleeping in. At the defined period, the device begins monitoring. Laying on ones back usually leads to snoring so if this position is detected via the orientation sensor, the metallic conductive material and electromagnet will remain engaged to prevent the user from snoring while they are on their back. If side or prone position is detected, the controller will de-energize the electromagnet to enable natural separation from metallic conductive plate which allows the mouth to open and air to flow through, relaxed muscles, and which prevents saliva buildup which are associated to discomfort.

The timer begins, as well as activating the second sensor, to monitor snoring intensity during the predetermined period of time. When snoring intensity exceeds a predetermined threshold or a supine position is detected during this time interval, the mouth is closed by charging the electromagnet to engage with metallic conductive plate. If a supine position or snoring is not detected, the system will remain disengaged for the duration of the defined time interval and then will engage to close the mouth. This marks a complete cycle, and the smart or intelligent oral appliance will adhere to this cycle throughout the night until arousal and the appliances 102 and 104 are removed by the individual. In addition, an option might include that data can be stored within the controller 116 or control circuit for post analysis of sleep quality. Additional sensors for monitoring sleep staging can be added for additional utility.

Based upon the above, according to an embodiment, a method for implementing control of an intelligent interactive oral appliance comprises providing a maxillary appliance configured to be releasably secured to an upper dentition; providing a mandibular appliance configured to be releasably secured to a lower dentition; providing at least one electromagnetic clamp that includes (i)(a) an electromagnet coupled to one of the maxillary or mandibular appliance and (i)(b) a metallic conductive material coupled to the other of the maxillary or mandibular appliance, wherein the electromagnetic clamp is configured to operate between (ii)(a) an engaged setting in which energization of the electromagnet produces a clamping action for electromagnetically engaging the metallic conductive material and (ii)(b) a disengaged setting in which de-energization of the electromagnet produces a non-clamping action for enabling the electromagnet to electromagnetically disengage from the metallic conductive material; providing a first sensor configured to detect at least one of a body position, a body orientation, a head position, a head orientation, or any combination of body and head positions or orientations; providing a second sensor configured to detect at least one of (i) a characteristic of sleep disordered breathing, (ii) a snoring intensity, or (iii) any combination thereof; providing a timer configured to provide one or more preset time intervals; and controlling, via a controller, an activation and a deactivation of the at least one electromagnetic clamp between the engaged setting and the disengaged setting, respectively, (i) to activate the at least one electromagnetic clamp and electromagnetically lock the maxillary appliance and mandibular appliance together for one or more air flow prevention cycles to prevent airflow through an oral cavity during use of the intelligent oral appliance in response to (i)(a) an initial powering ON of the intelligent oral appliance or (i)(b) detection of an engagement triggering event and (ii) to de-activate the at least one electromagnetic clamp and unlock the maxillary appliance from the mandibular appliance, respectively, for one or more periodic relaxation cycles in response to detection of a disengagement triggering event.

In a further embodiment, the method includes wherein the engagement triggering event comprises detection of one or more selected from the group consisting of a supine position, a snore intensity having an amplitude greater than a threshold, and expiration of a preset time interval, and wherein the disengagement triggering event comprises at least one of (i) detection of an upright position/orientation, and (ii) any combination of (a) no detection of a supine position, (b) no detection of a snore intensity having an amplitude greater than a threshold, (c) detection of a biological response to secretion or fluid buildup to a point that would be sensed for initiation of a cough or swallowing response action, or (d) no detection of expiration of the preset time interval, and wherein the preset time interval is a time interval that is reset upon (i) the initial powering ON of the intelligent oral appliance or (ii) the disengagement of the at least one electromagnetic clamp by a trigger other than detection of the upright position/orientation.

Accordingly, the embodiments of the present disclosure advantageously address the need to overcome comfort issues (i.e., the comfort issues associated with prior known appliances which are used to keep the mouth closed and that lead to discomfort from extended periods of closure) and may also lead to an improved therapy adherence on the part of the individual using the intelligent oral appliance 100. The embodiments of the present disclosure provide a means to allow for periodic relaxation periods in relationship to body/head position (associated to supine) and a controlled means to re-close the mouth that allows controlled intermittent muscle relief throughout the night with minimal disturbance to individual and/or his/her bed partner.

As disclosed herein, the embodiments make use of an intelligent interactive electronically powered oral appliance to keep a user's mouth closed to prevent airflow through the oral cavity in mouth breathers to aid in reduced snoring. The intelligent interactive oral appliance also allows for periodic relaxation cycles of the jaw muscle by uncoupling which reduces discomfort when locked in a single position for extended time periods. This periodic relaxation coordinates when the mouth is to open and monitors inputs in relation to body position. Timing of engagement is based on body position and/or pre-set time intervals. The periodic relaxation initiation may be aligned with an appropriate sleep stage to minimize any disruption to sleep quality. Furthermore, one or more additional sensor system monitors change of body position (to laying on back or supine) and optional vibration/sound of amplitude associated with beginning of snoring event to inform the controller to recouple and reengage the clamping that will bring the bottom and top dentitions or regions together to close the mouth.

In view of the above, a system comprising an electronically controlled battery powered electromagnetic clamp and control circuit contained within an oral appliance has been disclosed herein. The oral appliance responds to input from sensors and is fitted over the user's upper and lower teeth. The oral appliance is controlled in part by the activation of the electromagnet configuration (i.e., mounted to the sides and closer to the pivot of the jaw) via a position or orientation sensor that monitors body/head position. Body and head position determine the disengagement and engagement of the electromagnetic clamp for a predetermined time in order to minimize sleep disturbance. An additional sensor monitors the snoring intensity while disengaged and reengages when a threshold is exceeded for the next cycle. The electromagnetic clamp based oral appliance presents a means to keep the mouth closed to prevent air flow from moving through the mouth and also allows for controlled periods of disengagement of clamp mechanism to offset discomfort.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used in combination with POSA devices (e.g., respiratory support systems or devices) to supplement breathing through the mouth and disturbance to a bedpartner from snoring. The present disclosed embodiments can be used independently or together with a respiratory support system to overcome a pain point impacting reduced efficiency and adherence.

An addition application of the intelligent oral appliance of the present disclosure is for use by patients who need to use nasal masks (NIV, CPAP, HFNC, Supplemental Oxygen, etc.). Air leakage can occur if the mouth falls open while wearing the mask or cannula allowing for the therapeutic effect to be impacted by the undesired escape of gas flow or pressure. Still further, an additional application of the intelligent oral appliance of the present disclosure is to address Bruxism (teeth grinding) and providing a means in substituting another magnet in place of the metallic conductive plate to provide a repealing force to reduce stress on the jaw muscle and teeth grinding that lead to chronic headaches.

Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. An intelligent oral appliance comprising:
   a maxillary appliance configured to be releasably secured to an upper dentition;
   a mandibular appliance configured to be releasably secured to a lower dentition;
   at least one electromagnetic clamp coupled between the maxillary or mandibular appliances and configured to operate according to (i) an engaged clamping action in response to energization of the respective at least one electromagnetic clamp and (ii) a disengaged clamping action in response to de-energization of the respective at least one electromagnetic clamp;

a first sensor configured to detect at least one of a body position, a body orientation, a head position, a head orientation, or any combination of body and head positions or orientations;

a second sensor configured to detect at least one of (i) a characteristic of sleep disordered breathing, (ii) a snoring intensity, or (iii) any combination thereof;

a timer configured to provide one or more preset time intervals;

and a controller configured to control an activation and a deactivation of the at least one electromagnetic clamp between the engaged clamping action and the disengaged clamping action, respectively, (i) to activate the at least one electromagnetic clamp and electromagnetically lock the maxillary appliance and mandibular appliance together for one or more air flow prevention cycles in response to (i)(a) an initial powering ON of the intelligent oral appliance or (i)(b) detection of an engagement triggering event and (ii) to de-activate the at least one electromagnetic clamp and unlock the maxillary appliance from the mandibular appliance, respectively, for one or more periodic relaxation cycles in response to detection of a disengagement triggering event.

2. The appliance according to claim 1, wherein each electromagnetic clamp includes (i)(a) an electromagnet coupled to one of the maxillary or mandibular appliance at a posterior position thereof, and (i)(b) a metallic conductive material coupled to the other of the maxillary or mandibular appliance at a complementary posterior position thereof.

3. The appliance according to claim 2, wherein the engaged clamping action corresponds with the electromagnet of a respective electromagnetic clamp electromagnetically engaging with and being clamped to the metallic conductive material of the respective electromagnetic clamp, and wherein the disengaged clamping action corresponds with the electromagnet of the respective electromagnetic clamp no longer being clamped to, but electromagnetically disengaged from, the metallic conductive material of the respective electromagnetic clamp.

4. The appliance according to claim 2, wherein the electromagnet and the metallic conductive material of a respective electromagnetic clamp are each coupled on a same side of a respective maxillary or mandibular appliance at a posterior position thereof.

5. The appliance according to claim 2, wherein the electromagnet and the metallic conductive material of a respective electromagnetic clamp are each coupled to the maxillary or mandibular appliance at a posterior position thereof within a predetermined percentage of the total distance, back to front, from the posterior end of the respective maxillary or mandibular appliance.

6. The appliance according to claim 1, wherein the controller initiates (i) a first type of periodic relaxation cycle in alignment with a given sleep stage determined based upon one or more outputs of the first sensor, the second sensor, and the timer, and (ii) a second type of periodic relaxation cycle anytime within a sleep cycle based on the second sensor detecting (a) no snoring level activity or (b) a minimal snoring activity level or (c) one or more transient event needing relief, to allow de-activation of the electromagnetic clamp and unlock the maxillary appliance from the mandibular appliance and to allow, in the case of the transient event, momentary relief from a respective transient event.

7. The appliance according to claim 1, wherein the controller initiates a periodic relaxation cycle in alignment with a predetermined head, body, or head and body position or orientation.

8. The appliance according to claim 1, wherein the controller initiates the periodic relaxation cycle in response to one or more of (i) the first sensor detecting a predetermined head, body, or head and body position or orientation, (ii) the second sensor detecting a snore intensity less than a threshold intensity, and (iii) the at least one electromagnetic clamp not having been activated for a duration of at least a preset time interval, wherein the preset time interval is reset upon (i) the initial powering ON of the intelligent oral appliance or (ii) a de-activation of the at least one electromagnetic clamp by a trigger other than detection of an upright position/orientation.

9. The appliance according to claim 8, wherein the preset time interval is selected from the group consisting of fixed periods defined by a length of minutes, starting at 15 minutes up to a threshold time of no more than 60 minutes.

10. The appliance according to claim 8, wherein the predetermined head, body, or head and body position or orientation is a non-supine position.

11. The appliance according to claim 1, further comprising:

an additional sensor configured to detect a change in vibration or sound of a predetermined threshold amplitude associated with a beginning of a snoring event, and;

wherein the controller (a) terminates a given periodic relaxation cycle in response to detecting that the change in vibration or sound meets or exceeds the predetermined threshold amplitude associated with the beginning of the snoring event, and (b) subsequently re-activates the at least one electromagnetic clamp.

12. The appliance according to claim 11, further wherein the controller re-initiates the periodic relaxation cycle in response to (i) the electromagnetic clamp having not been re-activated during at least the preset time interval, and (ii) the first sensor detecting a head, body, or head and body position or orientation other than supine position.

13. The appliance according to claim 11, further comprising:

a power source adapted to provide power to the first, second, and additional sensors, the timer, and the controller.

14. The appliance according to claim 1, wherein the engagement triggering event comprises detection of one or more selected from the group consisting of a supine position, a snore intensity having an amplitude greater than a threshold, and expiration of a preset time interval, and wherein the disengagement triggering event comprises at least one of (i) detection of an upright position/orientation, and (ii) any combination of (a) no detection of a supine position, (b) no detection of a snore intensity having an amplitude greater than a threshold, (c) detection of a biological response to secretion or fluid buildup to a point that would be sensed for initiation of a cough or swallowing response action, or (d) no detection of expiration of the preset time interval, and wherein the preset time interval is a time interval that is reset upon (i) the initial powering ON of the intelligent oral appliance or (ii) the disengagement of the at least one electromagnetic clamp by a trigger other than detection of the upright position/orientation.

15. An intelligent oral appliance comprising:

a maxillary appliance configured to be releasably secured to an upper dentition;

a mandibular appliance configured to be releasably secured to a lower dentition;

at least one electromagnetic clamp that includes (i)(a) an electromagnet coupled to one of the maxillary or mandibular appliance and (i)(b) a metallic conductive material coupled to the other of the maxillary or mandibular appliance, wherein the electromagnetic clamp is configured to operate between (ii)(a) an engaged setting in which energization of the electromagnet produces a clamping action for electromagnetically engaging the metallic conductive material and (ii)(b) a disengaged setting in which de-energization of the electromagnet produces a non-clamping action for enabling the electromagnet to electromagnetically disengage from the metallic conductive material;

a first sensor configured to detect at least one of a body position, a body orientation, a head position, a head orientation, or any combination of body and head positions or orientations (body/head position);

a second sensor configured to detect at least one of (i) a characteristic of sleep disordered breathing, (ii) a snoring intensity, or (iii) any combination thereof;

a timer configured to provide one or more preset time intervals;

and a controller configured to control an activation and a deactivation of the at least one electromagnetic clamp between the engaged setting and the disengaged setting, respectively, (i) to activate the at least one electromagnetic clamp and electromagnetically lock the maxillary appliance and mandibular appliance together for one or more air flow prevention cycles in response to (i)(a) an initial powering ON of the intelligent oral appliance or (i)(b) detection of an engagement triggering event and (ii) to de-activate the at least one electromagnetic clamp and unlock the maxillary appliance from the mandibular appliance, respectively, for one or more periodic relaxation cycles in response to detection of a disengagement triggering event.

16. The appliance according to claim 15, wherein the engagement triggering event comprises detection of one or more selected from the group consisting of a supine position, a snore intensity having an amplitude greater than a threshold, and expiration of a preset time interval, and wherein the disengagement triggering event comprises at least one of (i) detection of an upright position/orientation, and (ii) any combination of (a) no detection of a supine position, (b) no detection of a snore intensity having an amplitude greater than a threshold, (c) detection of a biological response to secretion or fluid buildup to a point that would be sensed for initiation of a cough or swallowing response action, or (d) no detection of expiration of the preset time interval, and wherein the preset time interval is a time interval that is reset upon (i) the initial powering ON of the intelligent oral appliance or (ii) the disengagement of the at least one electromagnetic clamp by a trigger other than detection of the upright position/orientation.

17. The appliance according to claim 15, further comprising:

an additional sensor configured to detect a change in vibration or sound of a predetermined threshold amplitude associated with a beginning of a snoring event, and;

wherein the controller (a) terminates a given periodic relaxation cycle in response to detecting that the change in vibration or sound meets or exceeds the predetermined threshold amplitude associated with the beginning of the snoring event, and (b) subsequently re-activates the at least one electromagnetic clamp.

18. The appliance according to claim 17, further wherein the controller re-initiates the periodic relaxation cycle in response to (i) the electromagnetic clamp having not been re-activated for a duration of at least the preset time interval, and (ii) the first sensor detecting a head, body, or head and body position or orientation other than supine position.

19. A method for implementing control of an intelligent oral appliance, the method comprising:

providing a maxillary appliance configured to be releasably secured to an upper dentition;

providing a mandibular appliance configured to be releasably secured to a lower dentition;

providing at least one electromagnetic clamp that includes (i)(a) an electromagnet coupled to one of the maxillary or mandibular appliance and (i)(b) a metallic conductive material coupled to the other of the maxillary or mandibular appliance,;

wherein the electromagnetic clamp is configured to operate between (ii)(a) an engaged setting in which energization of the electromagnet produces a clamping action for electromagnetically engaging the metallic conductive material and (ii)(b) a disengaged setting in which de-energization of the electromagnet produces a non-clamping action for enabling the electromagnet to electromagnetically disengage from the metallic conductive material;

providing a first sensor configured to detect at least one of a body position, a body orientation, a head position, a head orientation, or any combination of body and head positions or orientations (body/head position);

providing a second sensor configured to detect at least one of (i) a characteristic of sleep disordered breathing, (ii) a snoring intensity, or (iii) any combination thereof;

providing a timer configured to provide one or more preset time intervals;

and controlling, via a controller, an activation and a deactivation of the at least one electromagnetic clamp between the engaged setting and the disengaged setting, respectively, (i) to activate the at least one electromagnetic clamp and electromagnetically lock the maxillary appliance and mandibular appliance together for one or more air flow prevention cycles to prevent airflow through an oral cavity during use of the intelligent oral appliance in response to (i)(a) an initial powering ON of the intelligent oral appliance or (i)(b) detection of an engagement triggering event and (ii) to de-activate the at least one electromagnetic clamp and unlock the maxillary appliance from the mandibular appliance, respectively, for one or more periodic relaxation cycles in response to detection of a disengagement triggering event.

20. The method according to claim 19, wherein the engagement triggering event comprises detection of one or more selected from the group consisting of a supine position, a snore intensity having an amplitude greater than a threshold, and expiration of a preset time interval, and wherein the disengagement triggering event comprises at least one of (i) detection of an upright position/orientation, and (ii) any combination of (a) no detection of a supine position, (b) no detection of a snore intensity having an amplitude greater than a threshold, (c) detection of a biological response to secretion or fluid buildup to a point that would be sensed for initiation of a cough or swallowing response action, or (d) no detection of expiration of the preset time interval, and wherein the preset time interval is a time interval that is reset upon (i) the initial powering ON of the intelligent oral appliance or (ii) the disengagement of the at least one electromagnetic clamp by a trigger other than detection of the upright position/orientation.

\* \* \* \* \*